(12) United States Patent
Alessa et al.

(10) Patent No.: US 11,950,975 B1
(45) Date of Patent: Apr. 9, 2024

(54) BAND SELECTION GUIDE FOR TEETH

(71) Applicant: KING SAUD UNIVERSITY, Riyadh (SA)

(72) Inventors: Noura Abdulaziz Alessa, Riyadh (SA); Reuof Abdulaziz Alessa, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/227,604

(22) Filed: Jul. 28, 2023

(51) Int. Cl.
*A61C 19/04* (2006.01)
*A61C 7/12* (2006.01)

(52) U.S. Cl.
CPC .............. *A61C 19/04* (2013.01); *A61C 7/12* (2013.01)

(58) Field of Classification Search
CPC .................................. A61C 19/04; A61C 7/12
See application file for complete search history.

(56) References Cited

U.S. PATENT DOCUMENTS

| | | | | |
|---|---|---|---|---|
| 650,389 A | * | 5/1900 | Hatfield | A61B 5/107 2/300 |
| 766,911 A | * | 8/1904 | Stemm | G01B 3/34 33/514.1 |
| 1,011,628 A | * | 12/1911 | Klein | A41H 1/02 33/759 |
| 1,233,131 A | * | 7/1917 | Schwartz | A61C 19/04 33/514 |
| 1,282,772 A | * | 10/1918 | Dinhofer | G01B 3/34 33/3 A |
| 2,231,121 A | | 2/1941 | Leopoldo | |
| 3,516,162 A | | 6/1970 | Ainsworth | |
| 3,889,382 A | * | 6/1975 | Husted | G01B 3/18 33/514 |
| 4,333,241 A | * | 6/1982 | Wasik | G01B 3/02 33/524 |
| 4,433,486 A | * | 2/1984 | Muehlenbein | G01B 3/008 33/760 |

(Continued)

FOREIGN PATENT DOCUMENTS

| | | | | |
|---|---|---|---|---|
| GB | 2099152 A | * | 12/1982 | A41H 1/02 |
| JP | 2011219908 A | | 11/2011 | |
| WO | 2004011873 A3 | | 2/2004 | |

OTHER PUBLICATIONS

Product/webpage: Ruiwaer 2pcs Baby Head Circumference Measuring Ruler PP Plastic Infant Head Circumference Tape 60cm 24 Inch Long.—Amazon.com.

*Primary Examiner* — Yaritza Guadalupe-McCall
(74) *Attorney, Agent, or Firm* — Nath, Goldberg & Meyer; Richard C. Litman

(57) ABSTRACT

A band selection guide is provided to help determine an exact size of a tooth, such as a molar, for example. The band selection guide is intended for single use and may be disposable. The band selection guide includes a tapered body having opposed proximal and distal ends, where the proximal end is larger than the distal end. A number of size markings appear on the tapered body near the distal end to indicate the size of a patient's tooth. A vertical slit is formed through the tapered body, such that the tapered body may be looped, with the distal end being inserted through the vertical slit. The band selection guide is placed around a tooth to be measured, with the size marking which aligns with the vertical slit indicating the size of the tooth.

10 Claims, 2 Drawing Sheets

(56) References Cited

U.S. PATENT DOCUMENTS

| | | | | |
|---|---|---|---|---|
| 4,441,258 A | * | 4/1984 | McDaniel | G01B 5/025 |
| | | | | 33/759 |
| 4,875,296 A | * | 10/1989 | Holzmeister | G01B 3/004 |
| | | | | 33/2 R |
| 4,920,659 A | | 5/1990 | Becher | |
| 5,212,871 A | | 5/1993 | Luccarelli | |
| 5,406,715 A | * | 4/1995 | Koizumi | G01B 3/1004 |
| | | | | 33/771 |
| 5,529,489 A | * | 6/1996 | Herrera | A61C 7/02 |
| | | | | 33/514 |
| D384,588 S | * | 10/1997 | Napier | D10/70 |
| 5,779,621 A | * | 7/1998 | Chaney | A61F 5/41 |
| | | | | 600/38 |
| 6,460,262 B1 | * | 10/2002 | Cabak | A61B 5/1076 |
| | | | | 33/759 |
| 6,467,180 B1 | * | 10/2002 | Chan | G01B 3/02 |
| | | | | 33/759 |
| 6,481,114 B1 | * | 11/2002 | Kalajian | A44C 9/02 |
| | | | | 33/544.4 |
| 6,640,460 B1 | * | 11/2003 | Nabarro | G01B 3/1004 |
| | | | | 33/759 |
| 6,817,110 B2 | * | 11/2004 | Bohnengel | G01B 3/1056 |
| | | | | 33/759 |
| 7,047,656 B1 | | 5/2006 | Parker | |
| 7,146,743 B2 | | 12/2006 | Oura | |
| 9,351,666 B2 | | 5/2016 | Wojcieszak et al. | |
| 2005/0072014 A1 | * | 4/2005 | Saunders | E21B 12/00 |
| | | | | 33/555.4 |
| 2009/0017420 A1 | | 1/2009 | Jabri | |
| 2015/0201866 A1 | * | 7/2015 | Wojcieszak | G01B 3/004 |
| | | | | 33/512 |

* cited by examiner

BAND SELECTION GUIDE FOR TEETH

BACKGROUND

Field

The disclosure of the present patent application relates to the field of orthodontics, and particularly to a tool for measuring tooth circumference to aid in the selection of orthodontic bands.

Description of Related Art

Orthodontic bands are widely used in the field of orthodontia, particularly with regard to orthodontic braces. While brackets are applied to most teeth to hold the orthodontic wires, bands are wrapped around the patient's molars. These bands have different sizes according to the tooth size and, in particular, circumference. Orthodontists typically determine the tooth size through trial and error by placing different band sizes on a tooth until a correct fit is found. This method of selection has several drawbacks. For example, the trial-and-error approach results in increased time through the repeated process of placing and removing a band on a particular tooth. Furthermore, the bands used for trial-and-error that are placed in a patient's mouth require sterilization in order to be re-used. The bands may also become damaged and require disposal, which results in wasted material. In addition, randomized trial-and-error sometimes leads to inaccuracy in selecting the correct band size, which could lead to complications for the patient wearing the band. Thus, a band selection guide solving the aforementioned problems is desired.

SUMMARY

The band selection guide includes a tapered body having opposed proximal and distal ends. The tapered body may be provided in the form of a thin, elongated strip made of a flexible material, such as stainless steel or the like. The proximal end of the tapered body may be larger than the distal end. Indicia is formed on the tapered body. The indicia is in the form of a plurality of graduated size markings representative of a size of a patient's tooth. The indicia is positioned closer to the distal end than the proximal end, and a vertical slit is formed through the tapered body, between the indicia and the proximal end.

In use, the distal end is inserted through the vertical slit to form a loop out of the tapered body. The looped band selection guide is placed around a tooth to be measured, such that the indicia are visible and face outwardly. The band selection guide is then tightened around the tooth. The circumference of the tooth can then be determined by visually observing the graduated size marking which is in alignment with, or is in closest alignment with, the vertical slit.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Embodiments of the band selection guide will be described below with reference to the drawings. The shape and size of the device is illustrated in the figures such that the device may be easily understood. Dimensions described herein are not necessarily shown to scale in the illustrated figures.

Figure 1:
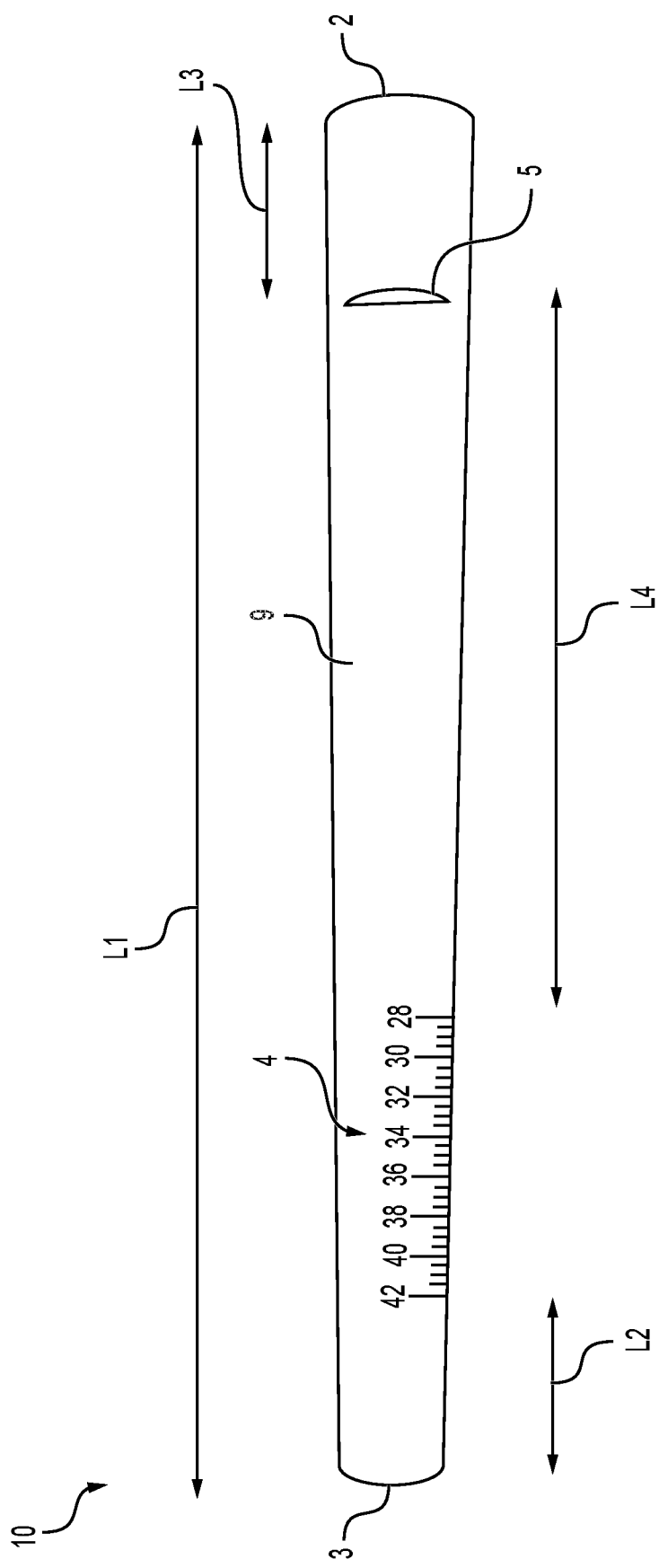
FIG. 1 is a front view of a band selection guide.

A band selection guide 10, is shown in FIG. 1. The band selection guide 10 may be used in pediatric dentistry and orthodontic clinics, as non-limiting examples. The band selection guide 10 may be made of a flexible stainless steel material, as a non-limiting example. As shown in FIG. 1, the band selection guide 10 has graduations, such as exemplary ruler markings 4, to help in determining the exact size of a tooth. The band selection guide 10 is intended for single-time use and may be disposable.

Figure 2:
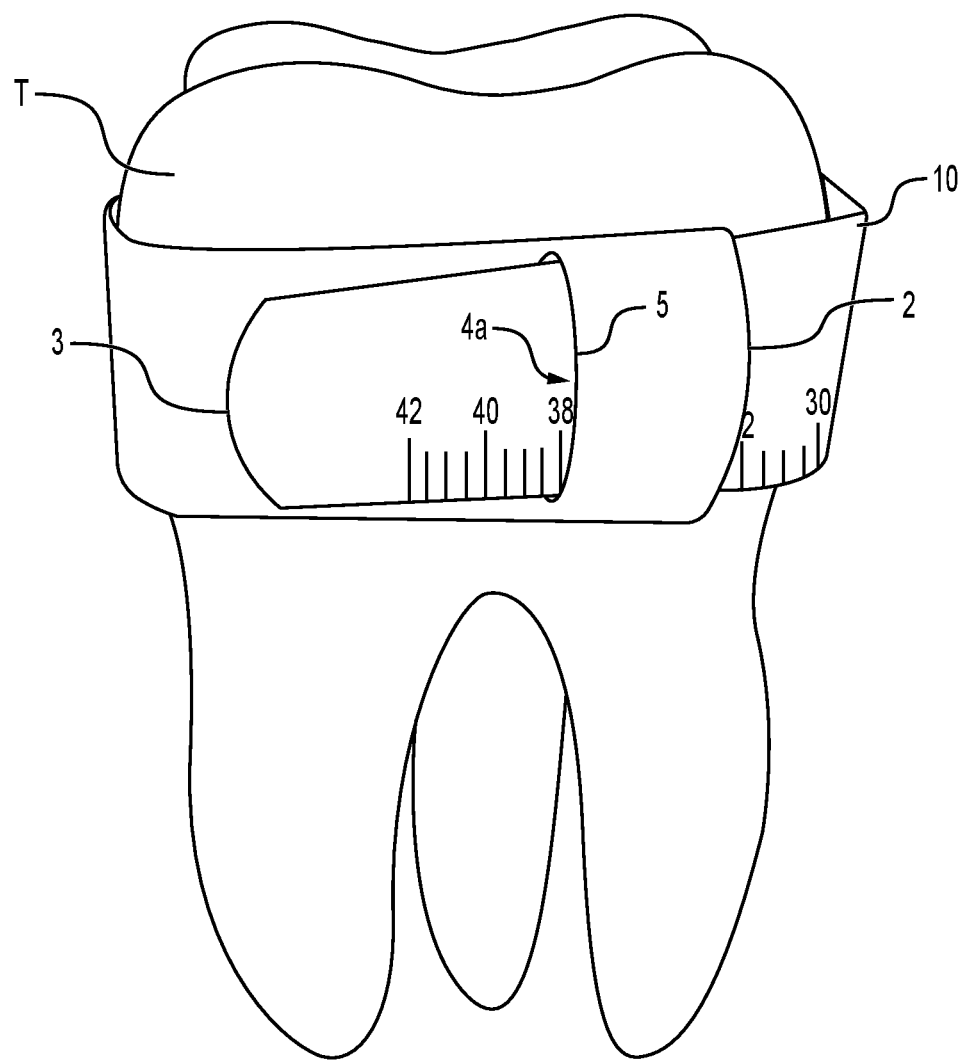
FIG. 2 is an environmental, perspective view of the band selection guide being used to measure the circumference of a tooth.

The band selection guide 10 has a tapered body 9 with opposed proximal and distal ends 2 and 3, respectively. As shown in FIG. 1, the proximal end 2 may be larger than the distal end 3. As noted above, a number of graduations, such as exemplary size markings 4, may be printed, etched or otherwise formed on the tapered body 9 near the distal end 3 to visually indicate the size of a patient's tooth. A vertical slit 5 is placed near the proximal end 2 for insertion of the distal end 3. As shown in FIG. 2, the tapered body 9 may be provided in the form of an elongated strip.

The size markings 4 may range from, as a non-limiting example, 28 mm to 42 mm and represent the size of an orthodontic band to be placed on a tooth, such as a molar, for example. In the non-limiting example of FIG. 1, only even numbers (28, 30, 32, . . . 42) are shown, which represent the longer ruler markings, while three short lines are provided between the longer numbered markings, such that the short lines represent half millimeter (0.5 mm) increments. It should be understood that the particular labeling of graduation 4, as well as its overall appearance and configuration, and its relative position to distal end 3 are all shown for exemplary purposes only and may be varied. Further, it should be understood that the shape and relative dimensions of tapered body 9 are also shown for exemplary purposes only and may be varied.

The band selection guide 10 may have an overall length L1 from the proximal end 2 to the distal end 3. The overall length L1 may be between, as a non-limiting example, 57 mm and 67 mm. The illustrated distance L2, from the size markings 4 to the distal end 3 may be between, as a non-limiting example, 10 mm and 15 mm. The distance L3, from the proximal end 2 to the vertical slit 5 may be between, as a non-limiting example, 5 mm and 10 mm.

In a non-limiting example, the proximal end 2 of the band selection guide 10 is approximately 8 mm in height and the distal end 3 is approximately 3 mm in height, while the distance L4 from the vertical slit 5 to the plurality of size markings 4 is approximately 28 mm.

A method of measuring the circumference of a tooth T using the band selection guide tool 10 is shown in FIG. 2. The method includes inserting the distal end 3 through the vertical slit 5 in the proximal end 2 of the band selection guide 10, thus forming a loop. The looped band selection guide 10 is then placed around a tooth T, as shown in FIG. 2, with the size markings 4 visible and facing outward. The proximal end 2 and distal end 3 may be grasped and tightened to create a secure fit of the band selection guide 10 around the tooth T being measured. To obtain the circumference size of the tooth T, the particular size marking (indicated as 4a in FIG. 2) in alignment with the vertical slit 5 is observed while the band selection guide 10 is tightly secured around the tooth T.

It is to be understood that the band selection guide is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A band selection guide, comprising a tapered body having opposed proximal and distal ends,
   wherein the proximal end is larger than the distal end,
   wherein indicia is formed on the tapered body, the indicia comprising a plurality of graduated size markings representative of a size of a patient's tooth,
   wherein the indicia is positioned closer to the distal end than the proximal end, and
   wherein a vertical slit is formed through the tapered body, the vertical slit being located between the indicia and the proximal end,
   wherein the distal end is inserted through the vertical slit to form a loop,
   wherein the band selection guide is configured to be placed around a tooth to be measured such that the indicia are visible and facing outwardly,
   wherein the band selection guide is configured to be tightened around the tooth to be measured, and
   wherein a circumference of the tooth is determined based on alignment between one of the graduated size markings and the vertical slit.

2. The band selection guide as recited in claim 1, wherein a distance between the proximal and distal ends is between 57 mm and 67 mm.

3. The band selection guide as recited in claim 1, wherein a distance from the indicia to the distal end is between 10 mm and 15 mm.

4. The band selection guide as recited in claim 1, wherein the graduated size markings range from 28 mm to 42 mm.

5. The band selection guide as recited in claim 1, wherein the tapered body is made of flexible stainless steel.

6. The band selection guide as recited in claim 1, wherein the proximal end is 8 mm in height and the distal end is 3 mm in height.

7. The band selection guide as recited in claim 1, wherein a distance from the proximal end to the vertical slit is between 5 mm and 10 mm.

8. The band selection guide as recited in claim 1, wherein a distance from the vertical slit to the indicia is 28 mm.

9. The band selection guide as recited in claim 1, wherein the band selection guide is disposable.

10. A method of measuring the circumference of a tooth, the method comprising:
    providing a band selection guide, the band selection guide comprising a tapered body having opposed proximal and distal ends, wherein the proximal end is larger than the distal end, wherein indicia is formed on the tapered body, the indicia comprising a plurality of graduated size markings representative of a size of a patient's tooth, wherein the indicia is positioned closer to the distal end than the proximal end, and wherein a vertical slit is formed through the tapered body, the vertical slit being located between the indicia and the proximal end;
    inserting the distal end through the vertical slit to form a loop;
    placing the band selection guide around a tooth to be measured, wherein the indicia are visible and facing outwardly;
    tightening the band selection guide around the tooth to be measured; and
    determining a circumference of the tooth based on alignment between one of the graduated size markings and the vertical slit.

* * * * *